US011419490B2

(12) United States Patent
Krimsky (10) Patent No.: US 11,419,490 B2
(45) Date of Patent: Aug. 23, 2022

(54) SYSTEM AND METHOD OF USING AN ENDOSCOPIC CATHETER AS A PORT IN LAPAROSCOPIC SURGERY

(71) Applicant: COVIDIEN LP, Mansfield, MA (US)

(72) Inventor: William S. Krimsky, Forest Hill, MD (US)

(73) Assignee: COVIDIEN LP, Mansfield, MA (US)

( * ) Notice: Subject to any disclaimer, the term of this patent is extended or adjusted under 35 U.S.C. 154(b) by 446 days.

(21) Appl. No.: 15/661,237

(22) Filed: Jul. 27, 2017

(65) Prior Publication Data

US 2018/0036084 A1 Feb. 8, 2018

Related U.S. Application Data

(60) Provisional application No. 62/369,986, filed on Aug. 2, 2016.

(51) Int. Cl.
*A61B 1/267* (2006.01)
*A61B 1/00* (2006.01)
(Continued)

(52) U.S. Cl.
CPC .......... *A61B 1/267* (2013.01); *A61B 1/00087* (2013.01); *A61B 1/00154* (2013.01);
(Continued)

(58) Field of Classification Search
CPC .............. A61M 16/04; A61M 16/0402; A61M 16/0404; A61M 16/0406; A61M 16/0409;
(Continued)

(56) References Cited

U.S. PATENT DOCUMENTS 5,135,490 A * 8/1992 Strickland ......... A61M 16/0858
604/48
6,188,355 B1 2/2001 Gilboa
(Continued)

FOREIGN PATENT DOCUMENTS

EP 2954849 A1 12/2015
WO 00/10456 A1 3/2000
(Continued)

OTHER PUBLICATIONS

European Search Report dated Jan. 3, 2018, corresponding to European Application No. 17184176.0; 8 pages.
(Continued)

*Primary Examiner* — Ryan N Henderson
(74) *Attorney, Agent, or Firm* — Carter, Deluca & Farrell LLP (57) ABSTRACT

A surgical system including an endoscopic navigation catheter, at least one laparoscopic access port, a laparoscopic tool, and an endoscopic tool. The endoscopic navigation catheter is configured for navigation of a luminal network to an area of interest. The at least one laparoscopic access port is placed adjacent to the area of interest. The laparoscopic tool is configured for insertion through the at least one laparoscopic access port, and the endoscopic tool is configured for insertion through the endoscopic navigation catheter. The laparoscopic tool and endoscopic tool enable a combined laparoscopic and endoscopic approach to the area of interest.

10 Claims, 9 Drawing Sheets

(51) Int. Cl.
   *A61B 17/34*   (2006.01)
   *A61M 16/04*   (2006.01)
   *A61B 34/10*   (2016.01)
   *A61B 34/20*   (2016.01)
   *A61B 1/018*   (2006.01)
   *A61B 17/00*   (2006.01)

(52) U.S. Cl.
   CPC .......... *A61B 1/018* (2013.01); *A61B 1/2676* (2013.01); *A61B 17/3421* (2013.01); *A61B 17/3423* (2013.01); *A61B 17/3474* (2013.01); *A61B 17/3478* (2013.01); *A61B 34/10* (2016.02); *A61B 34/20* (2016.02); *A61M 16/0404* (2014.02); *A61M 16/0486* (2014.02); *A61B 2017/00809* (2013.01); *A61B 2034/107* (2016.02); *A61B 2034/2051* (2016.02)

(58) Field of Classification Search
   CPC .......... A61M 16/0411; A61M 16/0415; A61M 16/0418; A61M 16/042; A61M 16/0422; A61M 16/0425; A61M 16/0427; A61M 16/0429; A61M 16/0431; A61M 16/0434; A61M 16/0436; A61M 16/0438; A61M 16/044; A61M 16/0443; A61M 16/0445; A61M 16/0447; A61M 16/045; A61M 16/0452; A61M 16/0461; A61M 16/0463; A61M 16/0475; A61M 16/0477; A61M 16/0479; A61M 16/0481; A61M 16/0484; A61M 16/0486; A61M 16/0488; A61M 16/049; A61M 16/0493; A61M 16/0495; A61M 16/0497; A61B 1/267; A61B 1/2673; A61B 1/2676; A61B 1/273; A61B 1/2733; A61B 1/2736; A61B 1/313; A61B 1/3132; A61B 1/0087; A61B 1/00135; A61B 1/00154; A61B 5/0421
   See application file for complete search history.

(56) References Cited

U.S. PATENT DOCUMENTS

| | | | |
|---|---|---|---|
| 6,287,290 B1* | 9/2001 | Perkins | A61M 16/0486 604/509 |
| 6,390,988 B1* | 5/2002 | Robinson | A61B 5/0813 600/529 |
| 6,398,775 B1* | 6/2002 | Perkins | A61M 1/85 604/102.03 |
| 6,585,639 B1* | 7/2003 | Kotmel | A61B 1/267 600/116 |
| 6,609,521 B1* | 8/2003 | Belani | A61M 16/0486 128/207.14 |
| 6,679,264 B1* | 1/2004 | Deem | A61F 2/04 128/912 |
| 6,709,401 B2* | 3/2004 | Perkins | A61M 16/0418 600/529 |
| 7,233,820 B2 | 6/2007 | Gilboa | |
| 8,137,302 B2* | 3/2012 | Aljuri | A61M 16/0404 604/24 |
| 8,409,168 B2* | 4/2013 | Wondka | A61B 17/12104 604/35 |
| 8,467,589 B2 | 6/2013 | Averbuch et al. | |
| 8,887,730 B2* | 11/2014 | Wood | A61M 16/0484 128/207.14 |
| 10,456,562 B2* | 10/2019 | Radhakrishnan | A61M 16/0404 |
| 2007/0203396 A1* | 8/2007 | McCutcheon | A61B 1/2676 600/173 |
| 2007/0225747 A1* | 9/2007 | Perkins | A61B 17/12104 606/191 |
| 2008/0051719 A1* | 2/2008 | Nair | A61B 5/4836 604/93.01 |
| 2008/0135052 A1* | 6/2008 | Bussieres | A61M 16/0418 128/207.15 |
| 2008/0228130 A1* | 9/2008 | Aljuri | A61M 16/0486 604/24 |
| 2009/0284255 A1 | 11/2009 | Zur | |
| 2011/0085720 A1 | 4/2011 | Averbuch | |
| 2011/0230974 A1* | 9/2011 | Musani | A61F 2/04 606/232 |
| 2011/0238083 A1* | 9/2011 | Moll | A61B 1/2676 606/130 |
| 2012/0024292 A1* | 2/2012 | Sandmore | A61M 16/0486 128/207.14 |
| 2012/0078055 A1* | 3/2012 | Berci | A61B 1/267 600/188 |
| 2012/0172664 A1* | 7/2012 | Hayman | A61B 1/0676 600/109 |
| 2012/0260921 A1* | 10/2012 | Sangwan | A61M 16/0486 128/207.14 |
| 2012/0302833 A1* | 11/2012 | Hayman | A61B 5/061 128/200.26 |
| 2012/0304984 A1* | 12/2012 | Curley | A61M 29/02 128/200.26 |
| 2013/0000635 A1* | 1/2013 | Curley | A61M 16/0472 128/200.26 |
| 2013/0025602 A1* | 1/2013 | Hayman | A61M 16/0484 128/207.15 |
| 2013/0053636 A1* | 2/2013 | Hayman | A61M 16/0459 128/207.14 |
| 2013/0096379 A1* | 4/2013 | Goldberg | A61M 16/0459 128/207.14 |
| 2013/0158351 A1* | 6/2013 | Daher | A61B 1/313 600/109 |
| 2013/0223702 A1 | 8/2013 | Holsing et al. | |
| 2014/0128672 A1* | 5/2014 | Daher | A61M 16/04 600/104 |
| 2014/0270441 A1 | 9/2014 | Baker | |
| 2015/0243042 A1 | 8/2015 | Averbuch et al. | |
| 2015/0305612 A1* | 10/2015 | Hunter | A61B 1/00009 600/109 |
| 2015/0351776 A1* | 12/2015 | Swayze | A61B 1/00087 600/104 |
| 2016/0000302 A1 | 1/2016 | Brown et al. | |
| 2016/0000414 A1 | 1/2016 | Brown et al. | |
| 2016/0038248 A1 | 2/2016 | Bharadwaj et al. | |
| 2016/0206301 A1* | 7/2016 | Radhakrishnan | A61M 16/0459 |
| 2017/0043111 A1* | 2/2017 | Hoftman | A61M 16/0445 |
| 2017/0072154 A1* | 3/2017 | Hoftman | A61M 16/0404 |

FOREIGN PATENT DOCUMENTS

| | | |
|---|---|---|
| WO | 01/67035 A1 | 9/2001 |
| WO | 2010/098871 A2 | 9/2010 |
| WO | 2016/004177 A1 | 1/2016 |

OTHER PUBLICATIONS

European Examination Report issued in corresponding EP Appl. No. 17 184 176.0 dated Jan. 17, 2020 (4 pages).
Extended European Search Report issued in corresponding application EP 21203781.6 dated Jan. 28, 2022 (10 pages).

* cited by examiner

SYSTEM AND METHOD OF USING AN ENDOSCOPIC CATHETER AS A PORT IN LAPAROSCOPIC SURGERY

CROSS REFERENCE TO RELATED APPLICATION

The present application claims the benefit of and priority to U.S. Provisional Application Ser. No. 62/369,986, filed on Aug. 2, 2016 the entire contents of which are incorporated herein by reference.

BACKGROUND

Technical Field

The present disclosure relates to surgical systems, and more particularly, to systems and methods of performing combined endoscopic and laparoscopic surgery.

Description of Related Art

It is a daily occurrence for people to enter a medical facility in order to be diagnosed or treated by a clinician for a multitude of different medical conditions. Paramount to proper treatment and diagnosis in some instances is the clinician's ability to target and sufficiently access an area of interest. Additionally, in most circumstances, clinicians strive to minimize the invasiveness of the medical procedure. This goal of minimal invasiveness limits a clinician's options in accessing the area of interest, and thus medical procedures and medical tools have been developed accordingly. Common methods for a minimally invasive treatment are surgeries performed using one or more access ports enabling the insertion of tools (e.g., graspers and ligation tools) as well as optics enabling the clinician to view the area being treated. Access ports come in a variety of styles and mechanisms using bladed, bladeless, and blunt obturator type trocars. Access ports often have at least one cannula enabling the insertion of tools and optics therethrough. The trocars are inserted into the cannula and the combination is inserted through a small opening or incision on the patient. Once placed, the trocar is removed from the cannula leaving the cannula available for the insertion of tools. For a given application, the trocar and cannulas may be formed of stainless steel, plastics, and a combination of the two.

One specialty access port that is often used for "single port" surgeries are marketed by Medtronic under the name SILS™ Ports. SILS™ Ports are surgically inserted in the umbilicus of the patient and are formed of an elastomeric material. In one example, three cannulas transcend the port, enabling the insertion of three different tools through a single opening in the patient, which is in a location where it will leave little or no observable scarring. Indeed, "single port" approaches to laparoscopy are major advances because of the limited number of incisions and thus decreased "invasiveness" quotient which generally improves the outcome for the patient.

A well-known laparoscopic thoracic surgery is the video-assisted thoracoscopic surgery (VATS). Typically during a VATS, a patient is intubated with a double lumen endotracheal tube, with each lumen orientated towards a different lung. In this manner, a clinician may induce atelectasis in the lung to be treated or operated upon and provide proper ventilation to the untreated lung. Following the placement of the double lumen endotracheal tube, a clinician creates one or more incisions in the chest wall for the placement of one or more access ports. Commonly, a clinician will make at least three incisions. In some instances, the chest wall may be pierced by an insufflation needle prior to the incisions. The typical size of an incision ranges from about 2 centimeters to about 6 centimeters. The exact placement of each incision depends upon the area of the lung that the clinician is seeking to access, but generally each incision will be placed within a space between two of the patient's ribs and in a complementary position to one another. The clinician can then place the access ports in each incision relying on the trocar to enlarge or create an opening into which the cannula will rest at the completion of the insertion.

The clinician will generally select one of the access ports for the insertion of a surgical camera and will select the other access ports for the insertion of surgical tools. In some instances, the camera may be inserted into the trocar prior to insertion of surgical tools to enable the clinician to observe the insertion process. The use of each access port may be interchangeable throughout the procedure. The camera inserted through the selected port transmits images of inside the patient's thoracic cavity onto a video monitor, providing guidance for the clinician. Once the clinician has located the area of interest using the surgical camera, surgical tools are inserted and navigated through respective access ports to undertake the necessary treatments. After the treatment is completed, the camera and surgical tools are removed, the access ports are removed, and the incisions in the patient are closed. Due to the more fixed nature of the chest cavity, i.e. the fixed and non-compliant nature of the ribs, in comparison to the abdomen or pelvis, the appropriate geometry of the inserted surgical tools with respect to one another is even more critical.

Another minimally invasive approach is the use of endoscopy to reach a desired location within the body via a natural orifice (e.g., nose, mouth or anus). Though not exclusively, endoscopic approaches are often employed in diagnostic (e.g., biopsy) procedures, to eliminate the need for making an incision into a patient, though endoscopes can and are inserted into a patient via a small incision in certain instances.

A specific type of endoscopy, bronchoscopy, is used to examine a patient's lungs and airways. After the placement of a bronchoscope, the clinician may insert other surgical devices through the bronchoscope to diagnose or to provide treatment to the patient.

Though both laparoscopy and endoscopy are both quite useful approaches to minimizing injury to patients caused by the surgery or diagnostic procedure, both procedures place limits on the ability of the clinician to access all of the areas of interest. Accordingly, improvements are always desirable and sought after.

SUMMARY

In accordance with the present disclosure, a surgical system includes an endoscopic navigation catheter, at least one laparoscopic access port, a laparoscopic tool, and an endoscopic tool. The endoscopic navigation catheter is configured for navigation of a luminal network to an area of interest. The at least one laparoscopic access port is placed adjacent to the area of interest. The laparoscopic tool is configured for insertion through the at least one laparoscopic access port, and the endoscopic tool is configured for insertion through the endoscopic navigation catheter. The laparoscopic tool and endoscopic tool enable a combined laparoscopic and endoscopic approach to the area of interest. The endoscopic tool is selected from a group consisting of a biopsy forceps, a cytology brush, an aspirating needle, an ablation catheter, and a camera. The laparoscopic tool is selected from a group consisting of a camera, a lung forceps, a surgical stapler, a vessel sealer, a collection bag, a morcellator, an ablation catheter, and a cautery device.

In an aspect of the present disclosure, the surgical system includes a double lumen endotracheal tube. The endoscopic navigation catheter is configured for placement within one of the lumens of the double lumen endotracheal tube. The endoscopic navigation catheter is configured as an internal port allowing manipulation of the area of interest. The surgical system further includes an electromagnetic sensor operatively associated with the endoscopic navigation catheter. In one embodiment, the electromagnetic sensor is formed on a locatable guide. In another embodiment, the endoscopic tool includes an electromagnetic sensor positioned on a distal portion of the endoscopic tool, and the distal portion is trackable by a tracking system. In yet another embodiment, the laparoscopic tool includes an electromagnetic sensor positioned on a distal portion of the laparoscopic tool, and the distal portion is trackable by a tracking system.

In one method of the present disclosure, a double lumen endotracheal tube is placed within a luminal network of a patient. An endoscopic navigation catheter is inserted within a lumen of the double lumen endotracheal tube and an endoscopic tool is inserted therethrough. One or more laparoscopic access ports are implanted proximally to an area of interest. A laparoscopic tool is inserting through at least one of the laparoscopic access ports, and a combined laparoscopic and endoscopic procedure is performed to the area of interest.

The method may include reviewing image data of the patient to identify the area of interest and planning at least one pathway to identified area of interest. The method also includes performing a survey to collect location data of the luminal network, wherein the survey utilizes the endoscopic navigation catheter and an electromagnetic sensor operatively associated therewith. The electromagnetic sensor is embodied on a locatable guide. The registration of the image data occurs before placement of the double lumen endotracheal tube within the luminal network of the patient. Additionally, navigating the endoscopic navigation catheter through the lumen of the double lumen endotracheal tube to the area of interest and removing the locatable guide including the electromagnetic sensor from the endoscopic navigation catheter. The laparoscopic tool is also navigated to the area of interest. An endoscopic procedure is performed with the endoscopic tool and a laparoscopic procedure is performed with the laparoscopic tool.

BRIEF DESCRIPTION OF THE DRAWINGS

Various aspects and features of the present disclosure are described hereinbelow with reference to the drawings, wherein.

DETAILED DESCRIPTION

The present disclosure is directed to a system and method which reduces the number of access ports required to perform a procedure, and utilized the best aspects of laparoscopic and endoscopic approaches to provide the same or greater level of access as traditional laparoscopic approaches as well as utilizing unique aspects of the endoscopic approaches to enable further tissue presentation, marker placement, treatment options, and other benefits to a patient and a clinician.

Described above are a variety of access ports including SILS™ Ports and other devices for achieving minimally invasive access to the patient's abdominal and thoracic cavities. However, single port approaches have limitations and this is certainly true in the chest. Indeed thoracic surgeons have had limited enthusiasm for the single port approach given the geometries involved with operating on the lungs and the chest. The use of a single port approach is further limited by the increasing prevalence of robotic surgical approaches which in general utilize smaller individual incisions but which enhance the geometry challenges associated with fewer ports. In fact, in a traditional three access port VATS or thoracoscopy (VATS)—one port is for the camera and the other two are for various instruments—typically to grasp and hold. A forth port is sometimes added as well to stabilize the tissue so that one can grasp and hold it more easily.

The challenges aside, one significant benefit of limiting the number of access ports is a reduction in neuro-praxias that occurs when the instruments place pressure on the nerves running along the inferior aspect of the ribs. Thus any reduction in the number of access ports being utilized to perform a procedure can have significant benefits to the patient and ease the challenges facing the clinician. Thus, by utilizing the functionality of an endoscope, or in the case of a VATS procedure, a bronchoscope, at least one and potentially more access ports can be eliminated from the procedure.

In the following description, surgical systems and methods of performing surgery will be described with reference to VATS and bronchoscopy procedures; however, a person skilled in the art would understand that these surgical systems and methods could be used for performing other types of surgeries employing both laparoscopic and endoscopic approaches.

Figure 1:
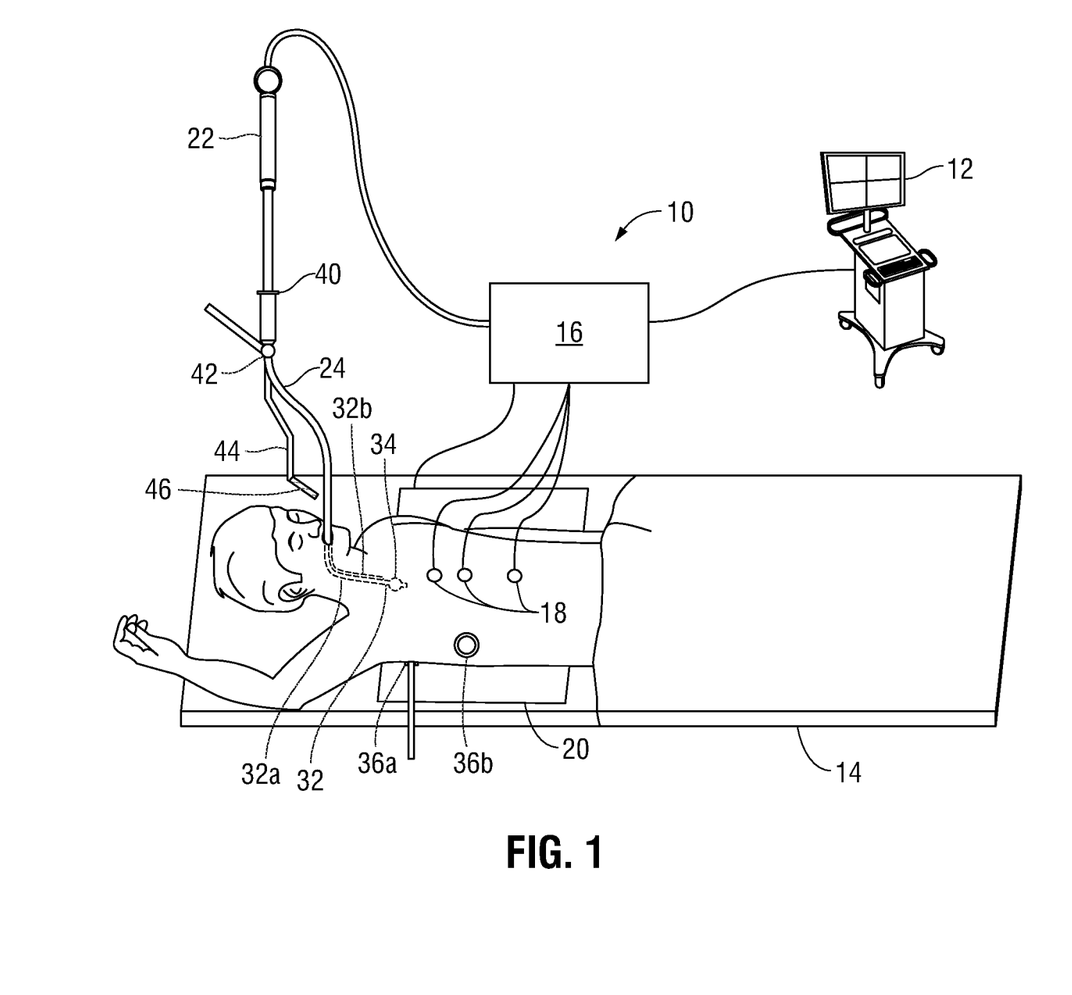
FIG. 1 is a perspective view of a surgical system provided in accordance with the present disclosure configured to perform a combined endoscopic and laparoscopic surgery.
Figure 2:
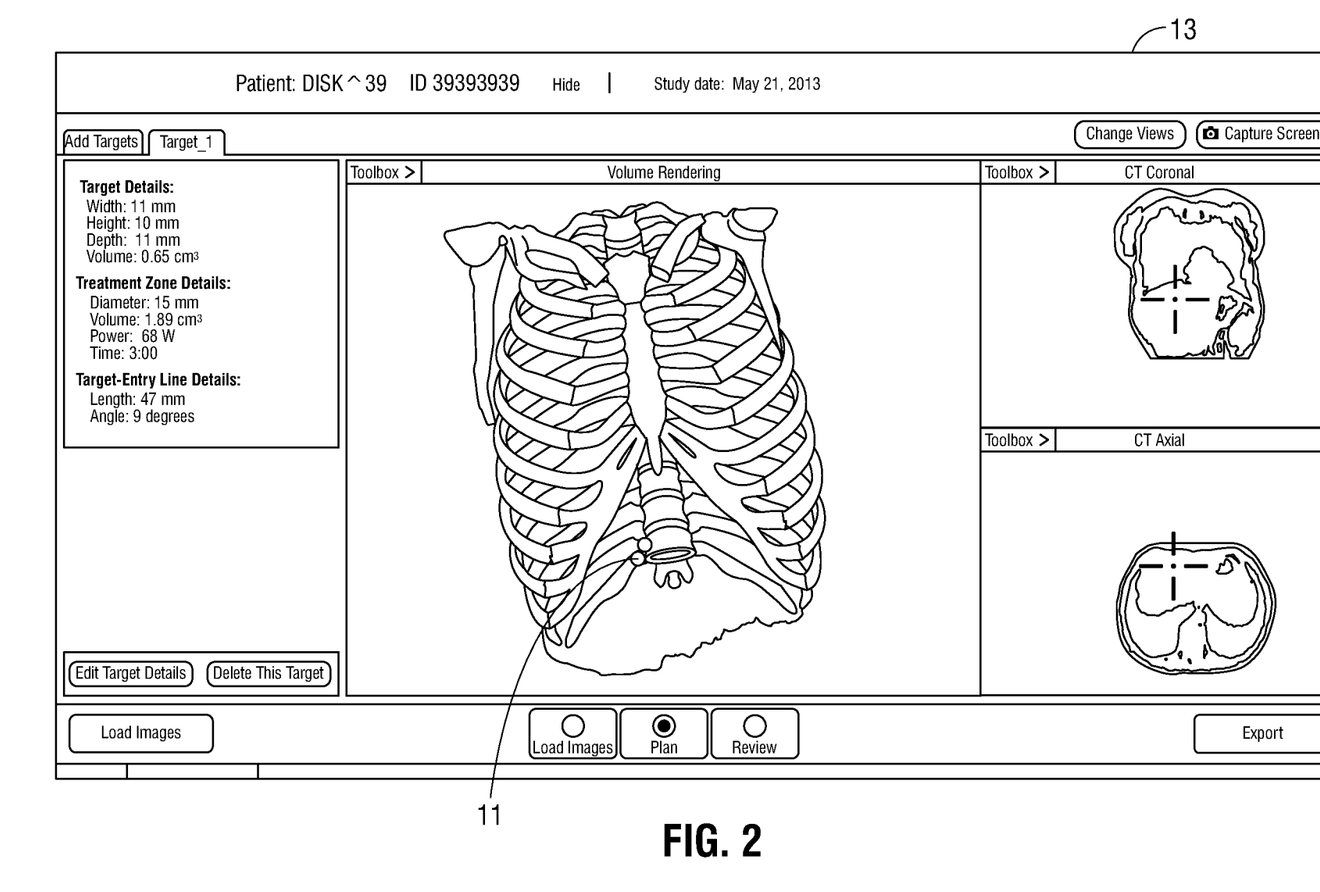
FIG. 2 is an illustration of a user interface presenting a view of reviewing a three-dimensional multi-layered model in accordance with an embodiment of the present disclosure.

The method of performing a combined laparoscopic and bronchoscopic VATS procedure is described herein to include four phases; however, each phase may be divided further to create an additional phase or phases may be combined. FIG. 1 depicts a surgical system 10 configured in part for reviewing image data to identify one or more areas of interest, and planning a pathway to an identified area of interest. This is referred to as a planning phase. Following successful planning, the surgical system 10 is employed in navigating an endoscopic navigation catheter to the area of interest, the navigation phase. Next, one or more endoscopic tools capable of performing a required task can be inserted into the endoscopic navigation catheter. This is the endoscopic phase. Finally or coincident with the endoscopic phase, the external placement of access ports adjacent the area of interest, and the use of laparoscopic tools through the access ports as well as the endoscopic tools placed through the endoscopic navigation catheter are utilized to treat a desired area of interest in the patient. This is the surgical phase. The planning, navigation, endoscopic, and surgical phases are all described in reference to an area of interest located within the thoracic cavity. However, all four phases may be performed when the area of interest is not located within the thoracic cavity.

Surgical system 10 generally includes an operating table 14 configured to support a patient "P"; a bronchoscope 24 configured for insertion through the patient's mouth "P's" and/or nose into the patient's "P's" airways; a double lumen endotracheal tube 32 configured for insertion through the patient's "P's" mouth into the patient's "P's" airways; a catheter guide assembly including a handle 22, an endoscopic navigation catheter 26, a locatable guide (LG) 28 including an electromagnetic sensor 30; laparoscopic access ports 36a, 36b placed proximal to an area of interest; endoscopic tools 50-90 insertable through endoscopic navigation catheter 26; laparoscopic tools 110-180 insertable through the laparoscopic access ports 36a, 36b; a work station 12 coupled to bronchoscope 24, endoscopic tools 50-90, and laparoscopic tools 110-180 for displaying video images received from bronchoscope 24, endoscopic tools 50-90 and laparoscopic tools 110-180, workstation 12 including software and/or hardware used to facilitate pathway planning and a user interface 13, identification of area of interest, navigation to area of interest, digitally marking the area of interest, and tracking LG 28 including sensor 30, endoscopic tools 50-90, and laparoscopic tools 110-180; a tracking system including a tracking module 16, a plurality of reference sensors 18, and a transmitter mat 20; a support system including a clamping member 46, an arm 44, a coupling mechanism 42, and a bronchoscope adapter 40.

As shown in FIG. 1 and indicated above, endoscopic navigation catheter 26 and LG 28 including sensor 30 are part of catheter guide assembly. In practice, the endoscopic navigation catheter 26 is inserted into bronchoscope 24 and double lumen endotracheal tube 32 for access to a luminal network of the patient "P." Specifically, endoscopic navigation catheter 26 of catheter guide assembly may be inserted into a working channel of bronchoscope 24 or a channel of double lumen endotracheal tube 32 for navigation through the patient's "P's" luminal network. The LG 28 including sensor 30 is inserted into the endoscopic navigation catheter 26 and locked in position such that the sensor 30 extends a desired distance beyond the distal tip of the endoscopic navigation catheter 26. The position and orientation (6 degrees-of-freedom) of the sensor 30 relative to the reference coordinate system, and the distal end of the endoscopic navigation catheter 26, within an electromagnetic field can be derived.

With respect to planning phase and surgical system 10 depicted in FIG. 1, a work station 12 utilizes a suitable imaged data for generating and viewing a three-dimensional model of the patient's "P's" airways, enables the identification of an area of interest on the three-dimensional model of the patient's "P's" airways (automatically, semi-automatically, or manually), and allows for determining a pathway through the patient's "P's" airways to the area of interest.

The planning phase may be performed in four separate sub-phases. In first sub-phase S1, suitable imaged data of patient "P" is generated using a suitable imaging device, such as MRI, ultrasound, CT scan, Positron Emission Tomography (PET), or the like, and the image data are stored within the memory coupled to work station 12.

In second sub-phase S2, a clinician may review the image data and select an area of interest. A software application may be initiated to enable review of the image data. More specifically, the CT scans are processed and assembled into a three-dimensional CT volume, which is then utilized to generate a three-dimensional model of the patient's "P's" airways. Techniques for generating a three-dimensional model are described in U.S. Patent Application Publication No. 2015-0243042 to Averbuch et al. entitled "Region-Growing Algorithm," filed May 12, 2015, the entire content of which is incorporated by reference herein. A planning software application may be initiated to enable the selection of the area of interest. The clinician will evaluate the three-dimensional model of patient's "P's" airways and will select the area of interest. The three-dimensional model may be manipulated to facilitate identification of the area of interest on the three-dimensional model or two-dimensional images, and selection of a suitable pathway through the patient's "P's" airways to access the area of interest can be made.

In a third sub-phase S3, using planning software the clinician creates the pathway to the area of interest. Finally, in the fourth sub-phase S4, the clinician reviews and accepts the pathway plan and may save the pathway plan, three-dimensional model, and images derived therefrom to work station 12 for use during the navigation phase, endoscopic phase, and surgical phase. The clinician may repeat either or both the second and third phases S2 and S3 as needed to select additional areas of interest and/or create additional pathways. For example, the clinician may select additional areas of interest and may create a pathway to each area of interest. The clinician may also or alternatively create multiple pathways to the same area of interest. One such planning software is the ILOGIC® planning suite currently sold by Medtronic. Details of such planning software are described in commonly owned pending U.S. Patent Application Publication No. 2014-0270441 to Matt W. Baker entitled "Pathway Planning System and Method," filed Mar. 15, 2013, the entire content of which is incorporated herein by reference.

In some embodiments, the planning phase may include an addition sub-phase 5. In sub-phase 5, the clinician may reference a three-dimensional multi-layered model 11 of the patient's "P's" anatomy to improve the pathways creating during sub-phase 3. The three-dimensional model, generated during the sub-phase 2, may provide the clinician with the three-dimensional multi-layered model 11 of the patient's "P's" anatomy including, for example, representation of the patient's "P's" skin, muscle, blood vessels, bones, airways, lungs, other internal organs, or other features of the patient's "P's" anatomy. The three-dimensional multi-layered model 11 allows the outer layer to be peeled back, removed, or adjusted to present a layer including the patient's "P's" ribs and layers including other anatomical features of the patient's "P's" internal anatomy to the clinician. The layers may be presented at different levels of opacity or transparency to allow the clinician to review the interior of the patient's "P's" torso relative to the area of interest. The three-dimensional multi-layered model 11 may be rotated by activating a user interface 13 including within work station 12 (FIG. 1) to peel back, remove, or adjust the opacity and translucence of each layer of the three-dimensional multi-layered model 11 to provide the clinician with a visual representation of the planned pathway to the area of interest relative to surrounding critical structures within the patient's "P's" body. For example, the clinician may use the user interface 13 to select specific layers to be presented in the three-dimensional multi-layered model 11 or to adjust the opacity or translucence of each individual layer. The three-dimensional multi-layered model is described in U.S. Patent Application Publication No. 2016-0038248 to Bharadwaj et al. entitled "Treatment Procedure Planning System and Method," filed Aug. 10, 2015, the entire content of which is incorporated by reference herein.

With respect to the navigation phase, a six degrees-of-freedom electromagnetic tracking system, e.g., similar to those disclosed in U.S. Pat. Nos. 8,467,589 and 6,188,355, and published PCT Application Nos. WO 00/10456 and WO 01/67035, the entire content of each of which is incorporated herein by reference, or other suitable positioning measuring system, is utilized for performing registration of the images, the pathway, and navigation, although other configurations are also contemplated. As indicated above, tracking system includes a tracking module 16, a plurality of reference sensors 18, and a transmitter mat 20. Tracking system is configured for use with LG 28 and particularly sensor 30. As described above, LG 28 including sensor 30 is configured for insertion through endoscopic navigation catheter 26 into a patient's "P's" airways (either with or without bronchoscope 24 or double lumen endotracheal tube 32) and are selectively lockable relative to one another via a locking mechanism.

Next, the navigation phase begins with patient "P" positioned on an operating table 14 which may be preceded by the administrating of general anesthesia. It is envisioned that patient "P" may be intubated immediately following sedation or intubated after registration, as detailed below. Depicted in FIG. 1, bronchoscope 24 is inserted within patient's "P's" mouth, and as described above, endoscopic navigation catheter 26 and LG 28 including sensor 30 is inserted into the bronchoscope 24 for access to patient's "P's" airways.

As shown in FIG. 1, transmitter mat 20 is positioned beneath patient "P." Transmitter mat 20 generates an electromagnetic field around at least a portion of the patient "P" within which the position of a plurality of reference sensors 18 and the sensor 30 can be determined with use of tracking module 16. For a detailed description of the construction of exemplary transmitter mats, which may also be referred to as location boards, reference may be made to U.S. Patent Application Publication No. 2009-0284255 to Zur entitled "Magnetic Interference Detection System and Method," filed Apr. 2, 2009, the entire content of which is incorporated by reference herein. One or more reference sensors 18 are attached to the chest of the patient "P." The six degrees-of-freedom coordinates of reference sensors 18 are sent to work station 12 (which includes the appropriate software) where they are used to calculate patient's "P's" coordinate frame of reference. Registration, as detailed below, is generally performed to coordinate locations of the three-dimensional model and two-dimensional images from the planning phase with the patient's "P's" airways as observed through the bronchoscope 24, and allow for the navigation phase to be undertaken with precise knowledge of the location of the sensor 30, even in portions of the airways where the bronchoscope 24 cannot reach. Further details of such a registration technique and their implementation in luminal navigation can be found in U.S. Patent Application Publication No. 2011-0085720, to Ron Barak et al entitled "Automatic Registration Technique," filed May 14, 2010, the entire content of which is incorporated herein by reference, although other suitable techniques are also contemplated.

Figure 3:
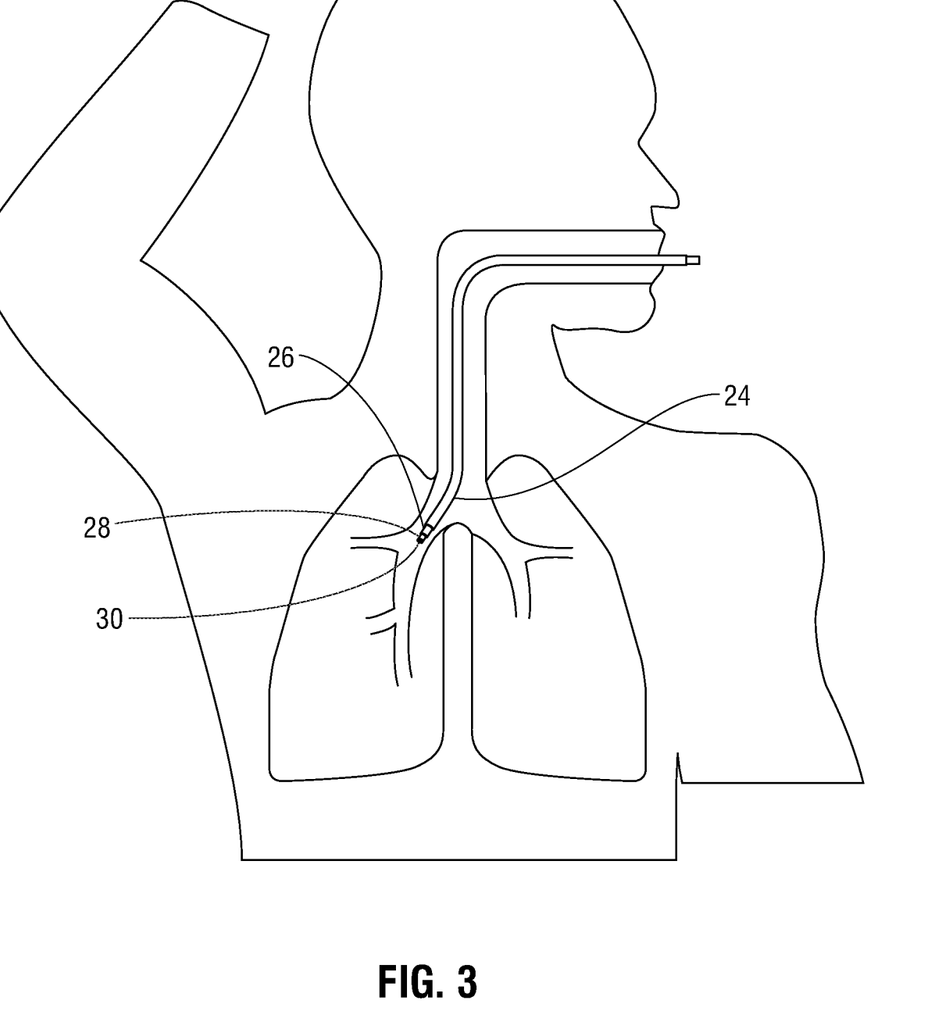
FIG. 3 is a front, cross-sectional, view of the lungs of a patient including a bronchoscope and a locatable guide including an electromagnetic sensor inserted therethrough.

As seen in FIG. 3, registration of the patient's "P's" location on the transmitter mat 20 is performed by inserting the bronchoscope 24 within the airways of patient "P" until a distal end of bronchoscope 24 can no longer traverse the airway (e.g., a dimension of bronchoscope 24 exceeds the airway), and inserting endoscopic navigation catheter 26 and LG 28 including sensor 30 within a working channel of bronchoscope 24 and moving LG 28 including sensor 30 through the airways of the patient "P." More specifically, data pertaining to locations of sensor 30, while LG 28 is moving through the airways, is recorded using transmitter mat 20, reference sensors 18, and tracking module 16. Rotation and translation of handle 22 of catheter guide assembly may facilitate maneuvering of a distal tip of LG 28, and in particular embodiments the endoscopic navigation catheter 26 may be angled or curved to assist in maneuvering the distal tip of the LG 28 through the patient's "P's" airways. It is also contemplated that registration of the patient's "P's" location on the transmitter mat 20 may be performed without the bronchoscope 24 and the endoscopic navigation catheter 26 and LG 28 including sensor 30 can be directly inserted within the airways of patient "P." In some embodiments, the distal tip of LG 28 may be maneuvered by a steering mechanism (not shown). The steering mechanism may include one or more elongated tension elements, such as steering wires. The steering wires are arranged in a manner such that the steering wire, when actuated, causes deflection of the tip. The steering mechanism and techniques for navigating are described in U.S. Pat. No. 7,233,820 to Pinhas Gilboa entitled "Endoscope Structure and Techniques for Navigating to a Target in Branched Structure," filed Mar. 29, 2003, the entire content of which is incorporated by reference herein.

A shape resulting from this location data is compared to an interior geometry of passages of the three-dimensional model generated in the planning phase, and a location correlation between the shape and the three-dimensional model based on the comparison is determined, e.g., utilizing the software on work station 12. In addition, the software identifies non-tissue space (e.g., air filled cavities) in the three-dimensional model. The software aligns, or registers, an image representing a location of sensor 30 with the three-dimensional model and two-dimensional images generated from the three-dimensional model, which are based on the recorded location data and an assumption that LG 28 including sensor 30 remains located in non-tissue space in the patient's "P's" airways. Alternatively, a manual registration technique may be employed by navigating the LG 28 including sensor 30 to pre-specified locations in the lungs of the patient "P," and manually correlating the images from the bronchoscope 24 to the model data of the three-dimensional model.

During registration, once the distal end of bronchoscope 24 is inserted to the farthest point possible within patient's "P's" airways, the bronchoscope 24 can be immobilized by the support system. As described above, the support system includes a clamping mechanism 46, an arm 44, a coupling mechanism 42, and a bronchoscope adapter 40. The support system may be utilized to secure bronchoscope 24 to a fixed structure within the operating theater. As depicted in FIG. 1, clamping mechanism 46 may be secured to operating table 14 with arm 44 extending vertical therefrom. Coupling mechanism 42 may be coupled to the bronchoscope 24, securing bronchoscope 24 to support system. Bronchoscope adapter 40 is connected to the bronchoscope 24 and support system, which allows endoscopic navigation catheter 26 to be inserted within bronchoscope 24 while bronchoscope 24 is being immobilized by support system.

Following registration of the patient "P" to the image data and pathway plan, the user interface 13 is displayed in the navigation software which sets the pathway that the clinician is to follow to reach the area of interest. One such navigation software is the ILOGIC® navigation suite currently sold by Medtronic. Details of such a navigation software are described in commonly owned and co-pending U.S. Patent Application Publication No. 2016-0000302, to Andrew E. Brown et al entitled "System and Method for Navigating within the Lung," filed Jun. 29, 2015, the entire content of which is incorporated herein by reference.

Figure 4:
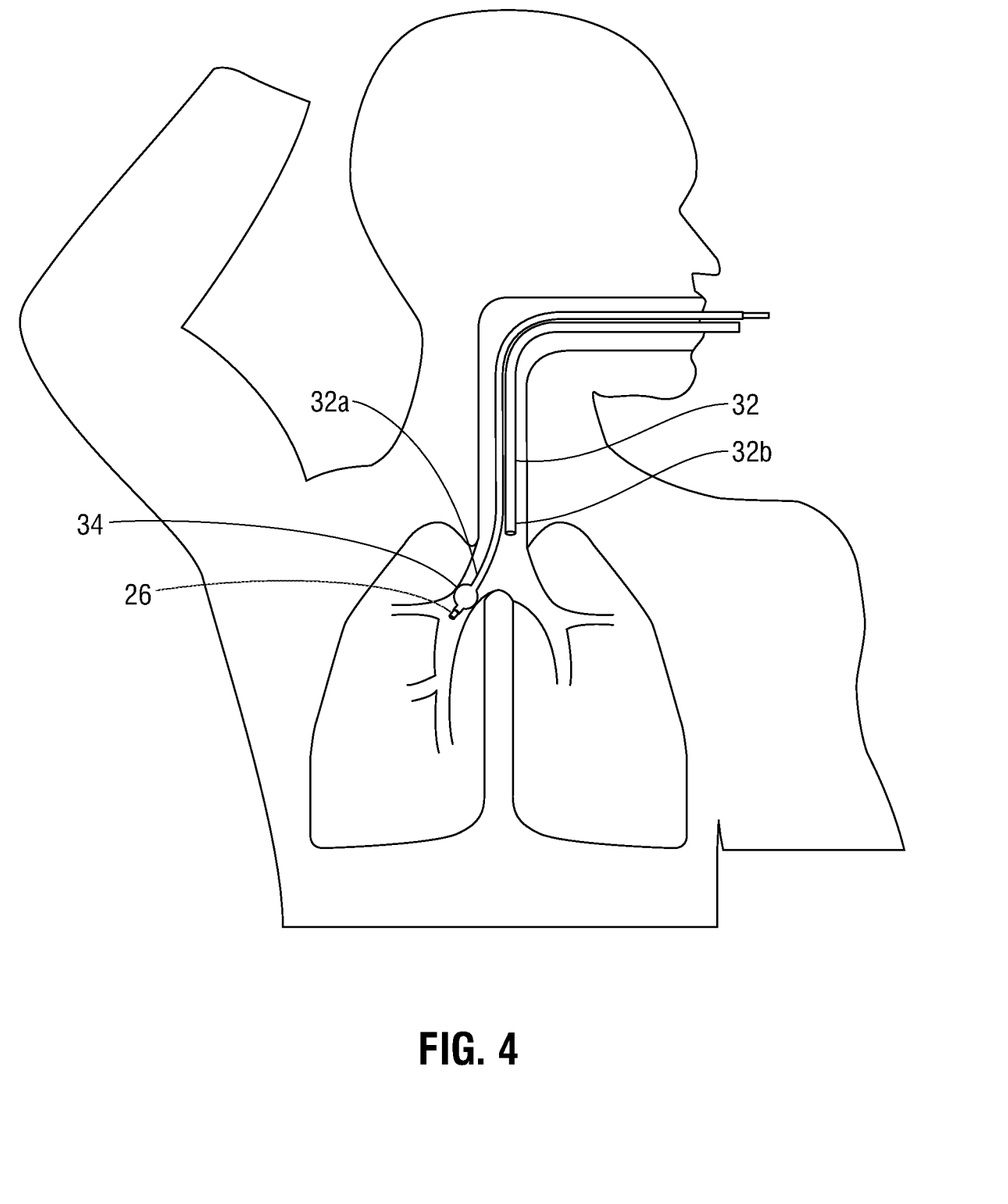
FIG. 4 is a front, cross-sectional, view of the lungs of a patient including a double lumen endotracheal tube and an endoscopic navigation catheter inserted therethrough.

As depicted in FIG. 4, upon completion of the registration, bronchoscope 24 may be removed from patient "P." In embodiments where patient "P" was not intubated prior to the placement of bronchoscope 24 or was intubated using a single lumen endotracheal tube, following the removal of bronchoscope 24, patient "P" will be intubated using double lumen endotracheal tube 32. The clinician will insert double lumen endotracheal tube 32 within the trachea of patient "P." It is envisioned that a clinician may insert bronchoscope 24 within one of lumens 32a, 32b of the double lumen endotracheal tube 32 for visual guidance in appropriately placing the double lumen endotracheal tube 32 within patient's "P's" airways. The images generated by bronchoscope 24 will be displayed by work station 12 or another suitable display may be configured to display images generated by bronchoscope 24. After appropriate placement of double lumen endotracheal tube 32, the bronchoscope 24 is removed. Endoscopic navigation catheter 26 including LG 28 with sensor 30 may then be placed within one of lumens 32a, 32b of the double lumen endotracheal tube 32 and navigated to the area of interest. The clinician may reference the three-dimensional images generated during the planning phase and the tracking system, which will track the movement of LG 28 including sensor 30, for guidance in navigating to the area of interest.

The initial navigational phase is completed upon successfully navigating the endoscopic navigation catheter 26 proximate the area of interest. Navigation phase may be initiated again to navigate to other selected areas of interest and/or to follow additional pathways. For example, the clinician may select additional areas of interest and may create a pathway to the same target. The clinician may also or alternatively create multiple pathways to the same area of interest of the initial navigating phase.

Commencement of each endoscopic phase and surgical phase is interchangeable. In some instances, the endoscopic phase and surgical phase may be initiated simultaneously. Termination of each endoscopic phase and surgical phase is also interchangeable. In some embodiments, each the endoscopic phase and surgical phase may be terminated simultaneously. It is also envisioned that endoscopic phase and surgical phase may be performed simultaneously. In embodiments where the endoscopic phase and surgical phase are performed simultaneously, both phases are performed in a manner that preserves the aseptic surgical site.

While performing the endoscopic phase and the surgical phase, the clinician may maneuver the working endoscopic tool 50-90 (FIGS. 6A-6E) and the working laparoscopic tool 110-180 (FIGS. 8A-8H) to avoid soiling and contamination of the aseptic surgical site. Additionally, the clinician may secure the working endoscopic tool 50-90 to the support system (FIG. 1) so that the working endoscopic tool 50-90 is appropriately positioned to avoid contamination of the area of interest while performing the required tasked. By securing the working endoscopic tool 50-90 to the support system, the clinician may transition within the sterile surgical field without risking cross-contamination. Further, the aseptic surgical site is preserved by the formation of one contamination vector. The one contamination vector extends between a proximal end of endoscopic navigational catheter 26 and the access ports 36a, 36b.

Atelectasis may be induced in patient's "P's" lung to be treated during either the endoscopic phase or the surgical phase. A clinician may determine the appropriate phase when to induce atelectasis. In some embodiments, atelectasis may be induced by means of a balloon included within the double lumen endotracheal tube 32 (FIG. 1) or other closure device disposed on an exterior surface thereof. In this manner, the double lumen endotracheal tube 32 including a balloon 34 would be employed to intubate the patient, as described above. Once the double lumen endotracheal tube 32 including a balloon 34 is appropriately placed, the balloon 34 may be inflated by means of a pump, syringe, or other suitable device in fluid communication therewith (not shown). As a result of the inflation, an exterior surface of the balloon 34 expands and compresses against the inner wall of the airway. In this manner, the treated lung is sealed off. It is contemplated that the air contained within the treated lung may be evacuated through a cannula defined through double lumen endotracheal tube 32 using any suitable means, such as a vacuum of the like (not shown), to induce atelectasis.

Figure 5:
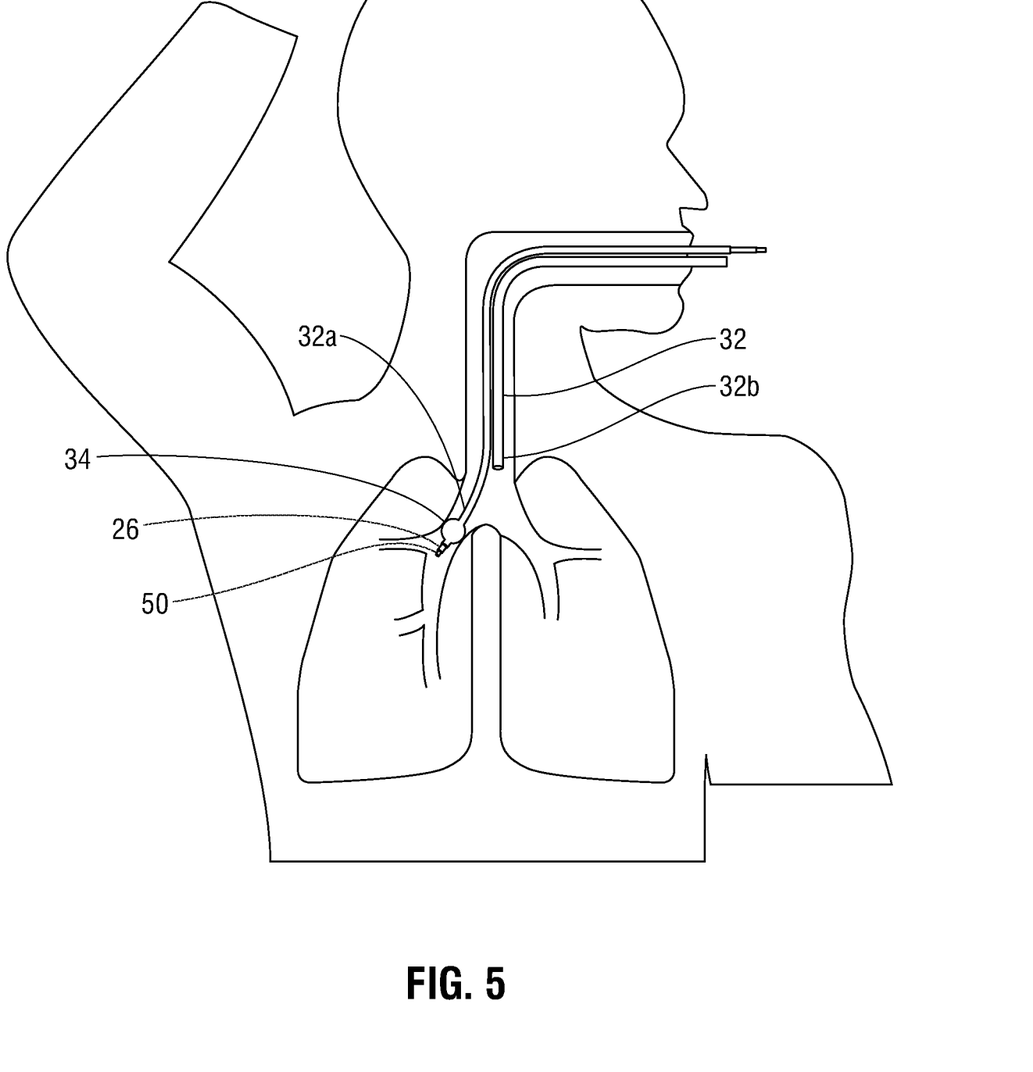
FIG. 5 is a front, cross-sectional, view of the lungs of a patient including a double lumen endotracheal tube, endoscopic navigation catheter, and an endoscopic tool.
Figure 6A:
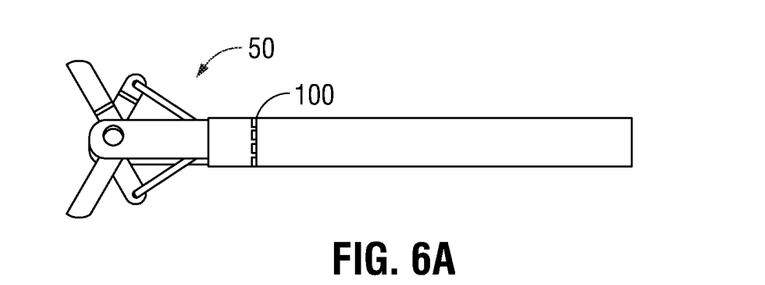
FIGS. 6A-6E are partial perspective views of the distal end portions of a plurality of different endoscopic tools in accordance with the present disclosure.
Figure 6B:
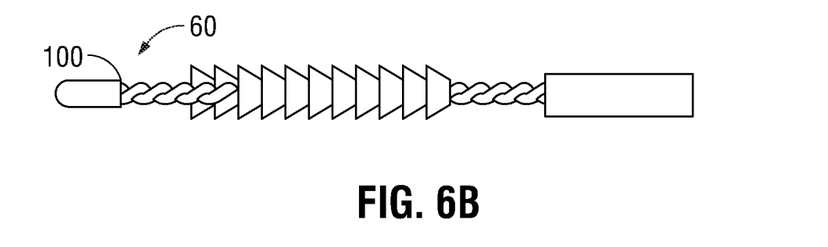
Figure 6C:
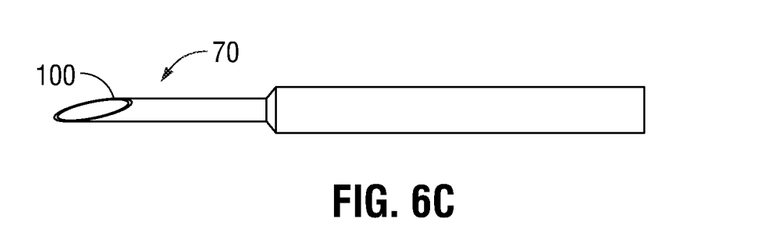
Figure 6D:
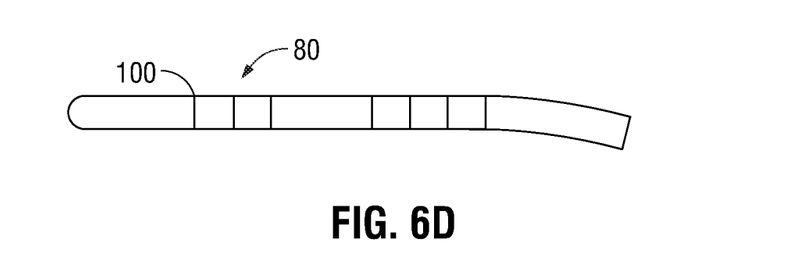
Figure 6E:
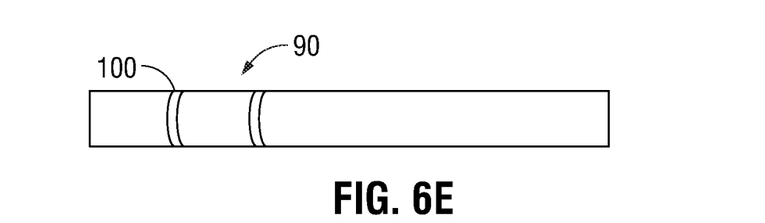

With respect to endoscopic phase depicted in FIG. 5, endoscopic tools, such as those depicted in FIGS. 6A-6E, including for example, biopsy forceps 50 (FIG. 6A), a cytology brush 60 (FIG. 6B), an aspirating needle 70 (FIG. 6C), an ablation catheter 80 (FIG. 6D), and a camera 90 (FIG. 6E) are inserted into endoscopic navigation catheter 26 and navigated to the area of interest for treatment and/or diagnosis of patient "P." It is also contemplated that any other suitable endoscopic tool may be used for treatment and/or diagnosis of patient "P."

The endoscopic phase may begin with unlocking and removing the LG 28 including sensor 30 from endoscopic navigational catheter 26. Removing LG 28 including sensor 30 leaves endoscopic navigation catheter 26 in place as a guide channel for guiding endoscopic tools 50-90 to the area of interest. Once endoscopic tools 50-90 are navigated proximately to the area of interest, endoscopic tools 50-90 may treat and/or diagnose the area of interest. Also, areas surrounding the area of interest may be treated by endoscopic tools 50-90.

It is envisioned that LG 28 including sensor 30 may be eliminated and endoscopic tools 50-90 are utilized for navigation, similarly as detailed above with respect to LG 28 with sensor 30. In this manner any of the above mentioned endoscopic tools 50-90 (FIGS. 6A-6E), may include a sensor 100 that, in conjunction with tracking system (FIG. 1), may be employed to enable tracking of a distal portion of endoscopic tools 50-90, as the distal portion of endoscopic tools 50-90 is advanced through the patient "P's" airways, as detailed above. Thus, with additional reference to FIG. 1, work station 12 or another suitable display may be configured to display the three-dimensional model and selected pathway, both of which were generated during the planning phase (as detailed above), along with the current location of the sensor 100 disposed in the distal portion of endoscopic tools 50-90 to facilitate navigation of the distal portion of endoscopic tools 50-90 to the area of interest and/or manipulation of the distal portion of endoscopic tools 50-90 relative to the area of interest.

Figure 7:
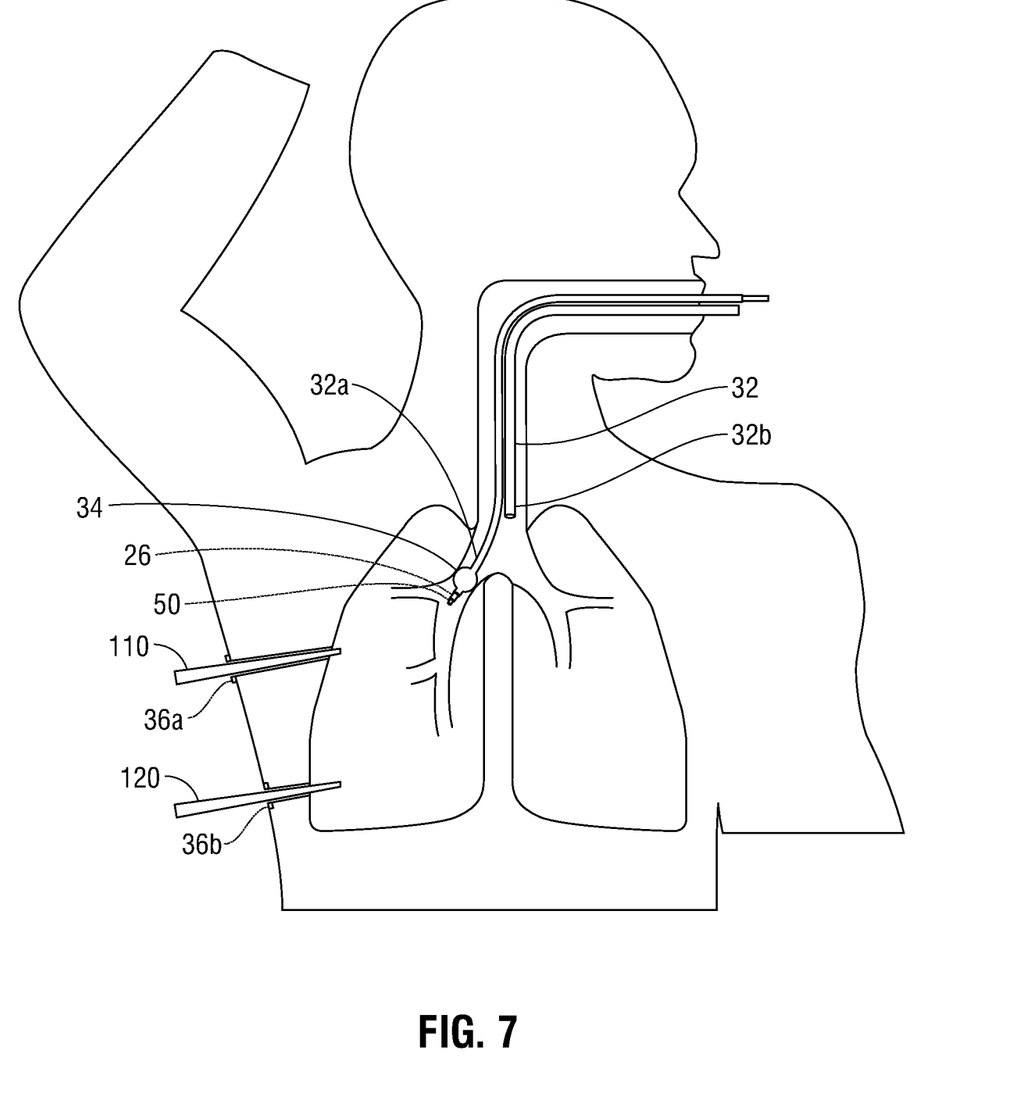
FIG. 7 is a front, cross-sectional, view of the lungs of a patient including a doubles lumen endotracheal tube, an endoscopic tool inserted into double lumen endotracheal tube, and laparoscopic tools inserted within external access ports.
Figure 8A:
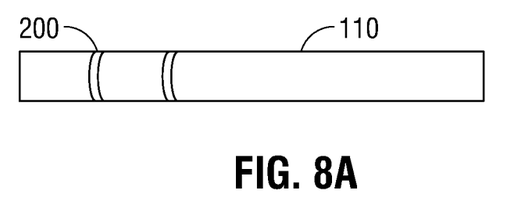
FIGS. 8A-8H are partial perspective views of the distal end portions of a plurality of different laparoscopic tools in accordance with the present disclosure.
Figure 8B:
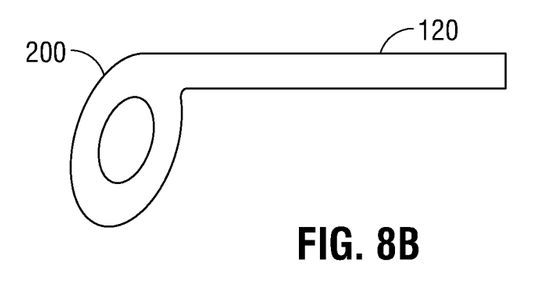
Figure 8C:
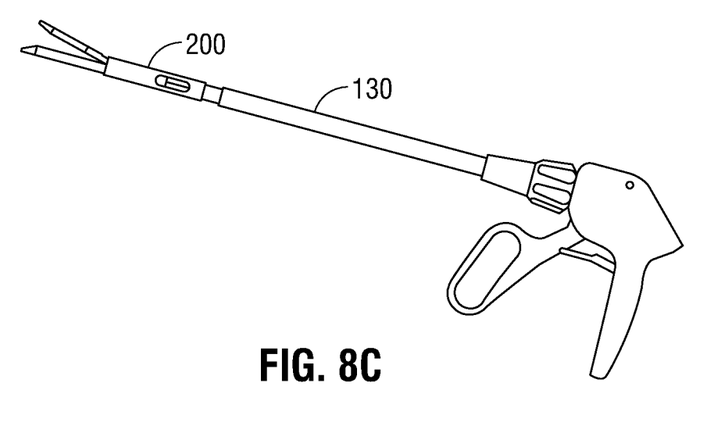
Figure 8D:
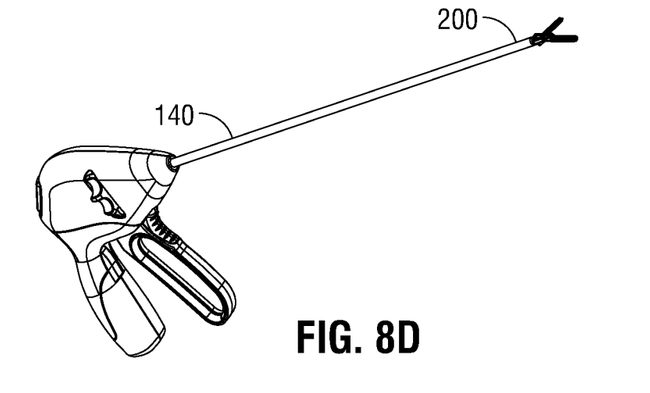
Figure 8E:
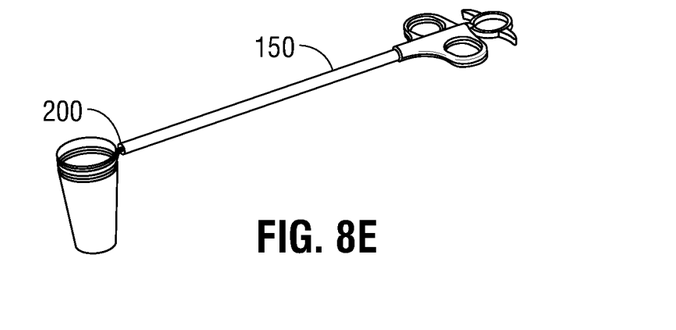
Figure 8F:
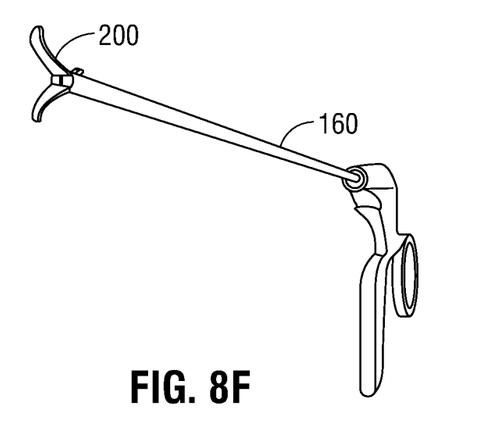
Figure 8G:
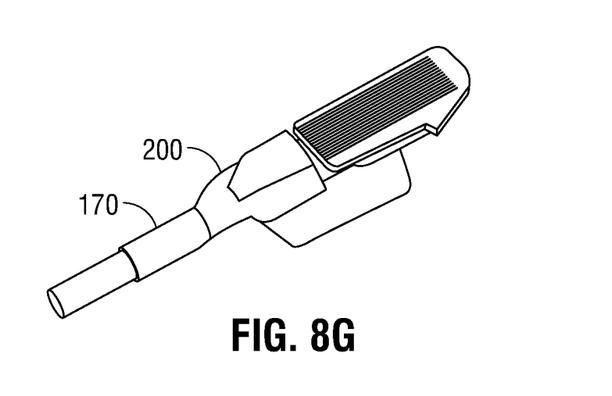
Figure 8H:
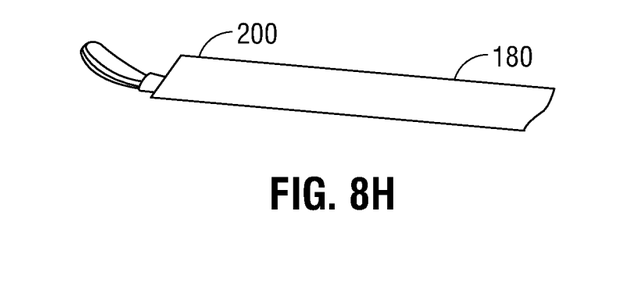

With respect to surgical phase depicted in FIG. 7, laparoscopic tools, such as those depicted in FIGS. 8A-8H, including for example, a camera 110 (FIG. 8A), a lung forceps 120 (FIG. 8B), a surgical stapler 130 (FIG. 8C), a vessel sealer 140 (FIG. 8D), a collection bag 150 (FIG. 8E), a morcellator 160 (FIG. 8F), an ablation catheter 170 (FIG. 8G), and a cautery device 180 (FIG. 8H) may be inserted into laparoscopic access ports 36a, 36b that are proximal to the area of interest and navigated to the area of interest for treatment of patient "P." It is also contemplated that any other suitable laparoscopic tool may be used for treatment of patient "P."

Referencing work station 12 and three-dimensional images generated during the planning phase (as detailed above), the clinician will implant laparoscopic access ports 36a, 36b (FIG. 7), as described above, approximately adjacent to the area of interest; however it is understood more or fewer ports may be implanted. Laparoscopic access ports 36a, 36b may be positioned to compliment endoscopic navigation catheter 26 and endoscopic tools 50-90.

Laparoscopic tools 110-180 are designed for insertion within laparoscopic access ports 36a, 36b. Camera 110 may initially be inserted within one of access ports 36a, 36b, allowing an internal visual display. The images generated by camera 110 will be displayed by work station 12 or another suitable display may be configured to display images generated by camera 110. A clinician may use the three-dimensional images generated during the planning phase and the images generated by camera 110 conjunctively for navigating the laparoscopic tools 110-180 to the area of interest and treating the area of interest. Additionally, it is envisioned that clinician may repeat sub-phase S2, S3 of planning phase to generate a pathway plan for inserting and navigating laparoscopic tools 110-180 to the area of interest.

Referring to FIGS. 8A-8H, laparoscopic tools 110-180 may include a sensor 200. In this manner, in addition to LG 28 including sensor 30 and endoscopic tools 50-90, laparoscopic tools 110-180 may be tracked with tracking system (FIG. 1). As a distal portion of laparoscopic tools 110-180 is advanced through the patient "P's" thoracic cavity, the sensor 200 enables tracking of the distal portion of laparoscopic tools 110-180, as detailed above. Thus, with additional reference to FIG. 1, work station 12, and/or any other suitable display may be configured to display the three-dimensional model and selected pathway, both of which were generated during the planning phase (as detailed above), along with the current location of the sensors 100, 200 disposed in the distal portion of endoscopic tools 50-90 and laparoscopic tools 110-180 to facilitate navigation of the distal portion of endoscopic tools 50-90 and laparoscopic tools 110-180 to the area of interest and/or manipulation of the distal portion of endoscopic tools 50-90 and laparoscopic tools 110-180 relative to the area of interest.

In some embodiments, the clinician may reference the layers of the three-dimensional multi-layered model 11, as described above, to improve the placement of access ports 36a, 36b. Also, clinician may reference the layers of the three-dimensional multi-layered model 11 to improve the navigation and movement of the endoscopic tools 50-90 and laparoscopic tools 110-180, which will enhance the effectiveness of the treatment for the patient "P" by promoting better navigation of endoscopic tools 50-90 and laparoscopic tools 110-180 to the area of interest.

Having inserted the endoscopic tools 50-90, placed the laparoscopic access ports 36a,36b, and inserted the laparoscopic tools 110-180 through the laparoscopic access ports 36a,36b, the clinician may now use both approaches to simultaneously manipulate, analyze, and treat the area of interest. For example, despite the best efforts of surgeons, identification of specific physiological structures of the lungs remains challenging. To assist in identifying structures, following navigation of a endoscopic navigation catheter 26 to an area of interest identified in the planning phase relying on the navigation system, a light source can be employed to illuminate the location such that the clinician can visualize the area of interest through a laparoscope inserted through one of the laparoscopic access ports 36a, 36b. Similarly, the endoscopic navigation catheter 26 inserted bronchoscopically may be used to deposit one or more markers, which can be identified using fluoroscopy or other imaging modalities to assist in the laparoscopic procedure. Similarly, the endoscopic navigation catheter 26 can be used to inject dyes or fluorescent materials at a target site enabling them to be better visualized by the clinician. Still further, following treatment laparoscopically (e.g., a lung resection or lobectomy), the bronchoscopically inserted endoscopic navigation catheter 26 may be used to inject one or more sealants to the area to assist in vessel closure and bleeding cessation. Similarly, an ultrasound probe (not specifically shown) may be used to interrogate tissue to confirm placement of the endoscopic navigation catheter 26 and the location of the area of interest. This might similarly be undertaken employing a fiber optic system inserted via the endoscopic navigation catheter 26 to interrogate the tissue. This interrogation could be either within the visible spectrum to provide visual tissue identification, or non-visible spectrum including infrared, ultraviolet, and others and may be used in combination with the use of dyes and fluorescent materials described above. Still further, combination treatments, e.g., microwave or chemical ablation can be undertaken bronchoscopically followed by traditional resection of the treated tissue. Yet another technique might employ cryo-ablation systems to freeze tissue, either lethally or sub-lethally, in order to promote vasoconstriction and limit blood flow to an area of interest to be treated.

Additionally, where the area of interest is concealed by other parts of the lungs, one or more of the endoscopic tools 50-90 may be employed bronchoscopically to capture tissue internally and move the concealing tissue (e.g., a portion of a lung lobe) to provide better access to the laparoscopic tools 110-180. The use of endoscopic navigation catheter 26 as an internal port allows repositioning/stabilization/maneuvering without the disadvantages associated with an additional external access port, and thus, the endoscopic navigation catheter 26 obviates the need for multiple external access ports. Also, the addition of an internal port may assist in alleviating the problem regarding a single-port VATS procedure and the geometries involved with operating on the lung and the chest cavity. To appropriately alleviate the geometric challenges associated with performing a single-port VATS within the chest cavity, the proper triangulation of the camera 110, access ports 36a, 36b, and endoscopic tools 50-90 should be achieved. The proper triangulation of camera 110, access ports 36a, 36b, and endoscopic tools 50-90 allows the clinician to properly manipulate the patient's "P's" tissue and avoid any unnecessary nerve damage often associated with laparoscopic procedures performed on the chest cavity. Additionally, combining laparoscopic access ports 36a, 36b and endoscopic navigation catheter 26 the clinician may have multiple views of the patient "P's" thoracic cavity. Work station 12 may be configured to receive the location data from tracking system and display the current location of all sensors on the three-dimensional model and relative to the selected pathway generated during the planning phase. Thus, navigation of endoscopic tools 50-90, LG 28 including sensor 30, and/or laparoscopic tools 110-180 to the area of interest and/or manipulation of laparoscopic tools 110-180 and endoscopic tools 50-90 relative to the area of interest, as detailed above, can be readily achieved. Work station 12 may be configured to have a multi-divided screen that simultaneously displays multiple views. Clinician may select a visual configuration of work station 12 to include combination of multiple views, such as, one configuration may display the three-dimensional images generated during the planning phase, tracking of endoscopic tools 50-90 and laparoscopic tools 110-180 within patient's "P's" airways, and the images generated by camera 110; another configuration may display the three-dimensional images generated during the planning phase, tracking of endoscopic tools 50-90 and laparoscopic tools 110-180 with patient's "P's" airways, and the images generated by camera 90; even another configuration may display the tracking of endoscopic tools 50-90 and laparoscopic tools 110-180 and the images generated by camera 110, and the images generated by camera 90; even another configuration may display the selected layer of the three-dimensional multi-layered model 11 generated during the planning phase; however, it is understood that work station 12 may include other visual configuration options for the clinician to choose.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A surgical system comprising:
   an endotracheal tube configured to be inserted into an airway of a patient, the endotracheal tube having a first tube defining a first lumen and a second tube defining a second lumen separate from the first lumen and having a length that is less than a length of the first lumen, the first tube configured to be inserted into a lung of the patient, one of the first or second lumens configured to receive a bronchoscope therein for placement of the endotracheal tube within the airway of the patient;
   an inflatable balloon disposed on the first tube and configured to compress against an inner wall of an airway within the patient's lung while the first tube is disposed within the patient's lung, wherein a distal end of the second lumen terminates within a trachea of the patient when the inflatable balloon compresses against the inner wall of the airway within the patient's lung, the second lumen configured to receive one of a biopsy forceps, a cytology brush, an aspirating needle, an ablation catheter, or a camera;
   an endoscopic navigation catheter defining a lumen and configured for insertion through the first lumen of the endotracheal tube for navigation of the endoscopic navigation catheter to an area of interest within the airway of the patient by extending the endoscopic navigation catheter distally from a distal end of the first lumen while the first tube is disposed within the patient's lung;
   at least one laparoscopic access port disposed through an incision in the patient in proximity to the area of interest;
   a laparoscopic tool configured for insertion through the at least one laparoscopic access port and into the airway of the patient, the laparoscopic tool having an electromagnetic sensor for tracking a location of a distal portion of the laparoscopic tool by an electromagnetic tracking system; and
   an endoscopic tool having an electromagnetic sensor for tracking a location of a distal portion of the endoscopic tool by the electromagnetic tracking system, the endoscopic tool configured for insertion through the lumen defined by the endoscopic navigation catheter while the endoscopic navigation catheter is extended distally of the distal end of the first lumen while the first tube is disposed within the patient's lung to guide the endoscopic tool to the area of interest within the airway of the patient during navigation of the endoscopic tool via the tracking system, wherein the laparoscopic tool is configured to be navigated within the airway of the patient to the area of interest via the tracking system to enable a combined laparoscopic and endoscopic treatment of the area of interest using the laparoscopic tool and the endoscopic tool.

2. The surgical system according to claim 1, further comprising an electromagnetic sensor operatively associated with the endoscopic navigation catheter.

3. The surgical system according to claim 2, further comprising a locatable guide insertable through the lumen defined by the endoscopic navigation catheter to guide the endoscopic navigation catheter to the area of interest, wherein the electromagnetic sensor is formed on the locatable guide and the locatable guide is configured to be removed from the lumen defined by the endoscopic navigation catheter prior to insertion of the endoscopic tool through the lumen defined by the endoscopic navigation catheter.

4. The surgical system according to claim 1, wherein the endoscopic navigation catheter is configured as an internal port allowing manipulation of the area of interest.

5. The surgical system according to claim 1, wherein the endoscopic tool is selected from a group consisting of a biopsy forceps, a cytology brush, an aspirating needle, an ablation catheter, and a camera.

6. The surgical system according to claim 1, wherein the laparoscopic tool is selected from a group consisting of a camera, a lung forceps, a surgical stapler, a vessel sealer, a collection bag, a morcellator, an ablation catheter, and a cautery device.

7. A surgical system, comprising:
   an endotracheal tube configured to be inserted into a patient's airway, the endotracheal tube having a first tube defining a first lumen and a second tube defining a second lumen separate from the first lumen and having a length that is less than a length of the first lumen, the first tube of the endotracheal tube configured to be inserted into a lung of the patient;
   an inflatable balloon disposed on the first tube and configured to compress against an inner wall of an airway within the patient's lung while the first tube is disposed within the patient's lung, wherein a distal end of the second lumen terminates within a trachea of the patient when the inflatable balloon compresses against the inner wall of the airway within the patient's lung, the second lumen configured to receive one of a biopsy forceps, a cytology brush, an aspirating needle, an ablation catheter, or a camera;

an endoscopic navigation catheter defining a lumen and configured for insertion through the first lumen of the endotracheal tube for navigation of the endoscopic navigation catheter to an area of interest within the airway of the patient by extending the endoscopic navigation catheter distally from a distal end of the first lumen while the first lumen is disposed within the patient's lung;

a laparoscopic access port in proximity to the area of interest;

a laparoscopic tool configured for insertion through the laparoscopic access port and into the airway of the patient, the laparoscopic tool having an electromagnetic sensor for tracking a location of the laparoscopic tool within the airway of the patient during navigation of the laparoscopic tool to the area of interest; and an endoscopic tool having an electromagnetic sensor for tracking a location of a distal portion of the endoscopic tool, the endoscopic tool configured for insertion through the lumen defined by the endoscopic navigation catheter while the endoscopic navigation catheter is extended distally of the distal end of the first lumen while the first tube is disposed within the patient's lung to guide the endoscopic tool to the area of interest within the airway of the patient during navigation of the endoscopic tool, wherein the laparoscopic tool is configured to be navigated within the airway of the patient to the area of interest to enable a combined laparoscopic and endoscopic treatment of the area of interest using the laparoscopic tool and the endoscopic tool.

8. The surgical system according to claim 7, wherein the first and second lumens are configured to receive at least one of the endoscopic navigation catheter or an endoscopic tool therethrough.

9. The surgical system according to claim 7, wherein the lumen defined by the endoscopic navigation catheter is configured to receive the endoscopic tool to guide the endoscopic tool to the area of interest while the endoscopic navigation catheter is extended distally of the distal end of the one of the first or second lumens through which the endoscopic navigation catheter is inserted and the one of the first or second lumens through which the endoscopic navigation catheter is inserted is disposed within the patient's lung.

10. A surgical system, comprising:

an endotracheal tube configured to be inserted into an airway of a patient, the endotracheal tube having a first tube defining a first lumen and a second tube defining a second lumen separate from the first lumen and having a length that is less than a length of the first lumen, wherein the first tube is configured to be inserted into a lung of the patient and a distal end of the second lumen terminates within a trachea of the patient;

an endoscopic navigation catheter defining a lumen and configured for insertion through the first lumen of the endotracheal tube for navigation of the endoscopic navigation catheter to an area of interest within the airway of the patient;

a laparoscopic access port disposed in proximity to the area of interest;

a laparoscopic tool configured for insertion through the laparoscopic access port and into the airway of the patient, the laparoscopic tool having an electromagnetic sensor for tracking a location of the laparoscopic tool within the airway of the patient during navigation of the laparoscopic tool to the area of interest; and an endoscopic tool having an electromagnetic sensor for tracking a location of a distal portion of the endoscopic tool, the endoscopic tool configured for insertion through the lumen defined by the endoscopic navigation catheter while the endoscopic navigation catheter is extended distally of a distal end of the first lumen while the first tube is disposed within the patient's lung to guide the endoscopic tool to the area of interest within the airway of the patient during navigation of the endoscopic tool, wherein the laparoscopic tool is configured to be navigated within the airway of the patient to the area of interest to enable a combined laparoscopic and endoscopic treatment of the area of interest using the laparoscopic tool and the endoscopic tool.

\* \* \* \* \*